United States Patent
Zhuang (10) Patent No.: US 9,918,707 B2
(45) Date of Patent: Mar. 20, 2018

(54) OCCLUSION DEVICE HAVING VARYING ANGLE FLAT DISK

(71) Applicant: Lifetech Scientific (Shenzhen) Co., Ltd., Shenzhen (CN)

(72) Inventor: Shaochun Zhuang, Shenzhen (CN)

(73) Assignee: Lifetech Scientific (Shenzhen) Co., Ltd. (CN)

( * ) Notice: Subject to any disclaimer, the term of this patent is extended or adjusted under 35 U.S.C. 154(b) by 403 days.

(21) Appl. No.: 14/765,102

(22) PCT Filed: Jan. 20, 2014

(86) PCT No.: PCT/CN2014/070929
§ 371 (c)(1),
(2) Date: Jul. 31, 2015

(87) PCT Pub. No.: WO2014/117661
PCT Pub. Date: Aug. 7, 2014

(65) Prior Publication Data
US 2015/0374350 A1    Dec. 31, 2015

(30) Foreign Application Priority Data
Feb. 4, 2013 (CN) .......................... 2013 1 0043462

(51) Int. Cl.
*A61B 17/08*    (2006.01)
*A61B 17/00*    (2006.01)
*A61B 17/12*    (2006.01)

(52) U.S. Cl.
CPC .... *A61B 17/0057* (2013.01); *A61B 17/12109* (2013.01); *A61B 17/12172* (2013.01);
(Continued)

(58) Field of Classification Search
CPC ...... A61B 17/0057; A61B 2017/00575; A61B 2017/00592; A61B 2017/00597; A61B 2017/00606; A61B 2017/00615
See application file for complete search history.

(56) References Cited

U.S. PATENT DOCUMENTS

2002/0068950 A1* 6/2002 Corcoran ........... A61B 17/0057
606/153
2002/0183787 A1* 12/2002 Wahr ................. A61B 17/0057
606/213

(Continued)

*Primary Examiner* — Jonathan Miles
(74) *Attorney, Agent, or Firm* — Raymond Sun (57) ABSTRACT

Disclosed is an occlusion device having an angle variable flat disk, comprising a single-layer disk (4), a plug (6) and a waist (5) connecting the single-layer disk (4) and the plug (6). The single-layer disk (4) is braided from elastic strands and comprises a plurality of radially-arranged support rods (40). Grids braided from elastic strands are provided on the surface of the plug (6). The waist (5) comprises at least one connecting strand. An annular interlocking structure is provided in the center of the single-layer disk (4). The plurality of support rods (40) are connected into a flat integral body via the annular interlocking structure. The connecting strand of the waist (5) is connected to the annular interlocking structure and the grids of the plug (6). The occlusion device has the features of a flat single-layer disk and a flexible waist structure at the same time, and the single-layer disk has the function of adaptive regulation of morphology and is able to effectively adapt to different physiological structures while reducing complications.

21 Claims, 6 Drawing Sheets

(52) U.S. Cl.
CPC .......... *A61B 2017/00575* (2013.01); *A61B 2017/00592* (2013.01); *A61B 2017/00597* (2013.01); *A61B 2017/00606* (2013.01); *A61B 2017/00615* (2013.01); *A61B 2017/1205* (2013.01)

(56) References Cited

U.S. PATENT DOCUMENTS

| | | | |
|---|---|---|---|
| 2011/0066180 A1* | 3/2011 | Zeng | A61B 17/0057 606/213 |
| 2012/0071918 A1* | 3/2012 | Amin | A61B 17/0057 606/213 |
| 2012/0078295 A1* | 3/2012 | Steiner | A61B 17/0057 606/213 |
| 2015/0039084 A1* | 2/2015 | Levi | A61B 17/0057 623/2.38 |

* cited by examiner

OCCLUSION DEVICE HAVING VARYING ANGLE FLAT DISK

TECHNICAL FIELD

The present invention relates to a medical instrument, in particular to an instrument for occluding channels or defects or openings in a human body, especially occlusion devices suitable for Patent Foramen Ovale (PFO), and also for occluding patent ductus arteriosus, atrial septal defect, ventricular septal defect, etc.

BACKGROUND OF THE INVENTION

The method for treating congenital heart diseases by transcatheter intervention has been widely accepted at present. In comparison to the conventional surgical therapy, the method has obvious advantages, mainly embodies in less trauma and fast recovery.

For example, the principle of treating Atrial Septal Defect (ASD) by transcatheter intervention is as follows: an elastic occlusion instrument is compressed into a small-size or a narrow and long shape and then conveyed to a defect position through a conduit, and then the elastic occlusion instrument is self-expanded to a preset shape, where the preset shape often includes two disks and a connecting component connecting the two disks. The two disks are disposed on two sides of the defect to occlude the defect. Such occlusion instrument is often called an occluder or an occlusion device.

Early disk is made from highly rigid metal. In a heart, such disk will bear cyclic stress action caused by heartbeat, so many occlusion instruments will be fractured due to fatigue stress.

An occlusion device braided from a plurality of fine metal wires (hereinafter referred to as a braided occlusion device) has been developed. On one hand, as the braiding strands are fine and flexible and generate a small stress due to deformation along with heartbeat, the ability to resist fatigue fracture is obviously improved; on the other hand, in such occlusion devices formed by a plurality of braiding strands, even though a few strands are cracked, the crack does not easily spread to other portions of the disk, so the whole device has good fatigue resistance. Although there still are some disadvantages, such a braided occlusion device has a good clinical manifestation as a whole when applied in the occlusion of Atrial Septal Defect (ASD). However, when a similar design is applied in the occlusion of Patent Foramen Ovale (PFO), new disadvantages are manifested. A main distinction between the atrial septal defect and the patent foramen ovale in the physiological structure lies in that the atrial septal defect looks like an obvious gap or a porous structure in shape, while the patent foramen ovale looks more like a channel having an overlapped portion. Due to this characteristic, occlusion devices for occluding patent foramen ovale require a more flexible connecting structure.

Figure 1:
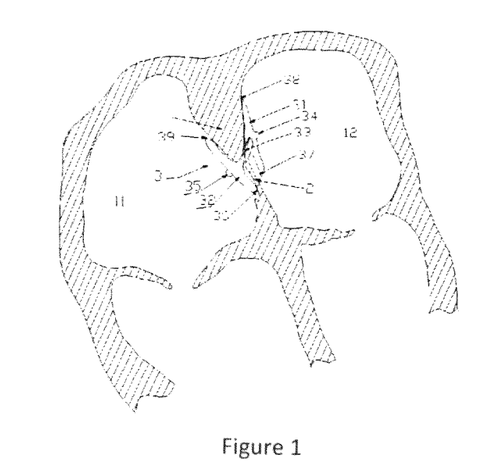
FIG. 1 is a cross-sectional diagram of a cardiac four-chamber structure.

FIG. 1 is a cross-sectional diagram of four chambers of a heart. The channel of PFO is located between a right atrium 11 and a left atrium 12, and an occlusion device is placed at this position. The anatomical structure of patent foramen ovale differs from that of a common atrial septal defect. The patent foramen ovale looks more like a narrow and long channel than a porous defect, and a septum secundum 1 and a septum primum 2 between the left atrium and the right atrium are partially overlapped. For most people, after growth and development, at the overlapped position of the septum secundum 1 and the septum primum 2, both will be merged as one so as to separate the left atrium from the right atrium. If the overlapped portion fails to be merged, a channel communicating the left atrium and the right atrium is formed, and this channel is called patent foramen ovale. Due to a large individual difference, the anatomical structure near the patent foramen ovale is mainly embodied in the difference in thickness of an atrial spectrum, for example, the thickness of the septum secundum 1. In some individuals, the average thickness of the septum secundum 1 may be 2 mm; while in other individuals, the average thickness of the septum secundum 1 may be 8 mm.

The common occlusion method for patent foramen ovale is to implant an occlusion device having two disk-shaped structures (hereinafter referred to as disks), as disclosed in CN0719448.1. In the double-disk occlusion device 3 in FIG. 1, a first disk 31 and a second disk 32 tightly holds two atrial spectra (including a septum secundum 1 and a septum primum 2) which are not completely fitted, and then the two disks are connected via a waist connecting structure 33 (hereinafter referred to as a waist) so as to fit the atrial spectra. After the occlusion device is implanted, endothelium will grow gradually and finally wrap the whole double-disk occlusion device 3 until a radical occlusion is formed.

In ideal conditions, after an occlusion device is implanted, the first disk 31 and the second disk 32, which are disposed on two sides of PFO, respectively, are closely clung to walls on two sides of the atrial spectra. In an atrium, a portion of the disk closely clung to the atrial wall is easily and quickly covered by endothelial cells, while a protrusion portion 34 on the first disk and a protrusion portion 35 on the second disk take more time to be covered, and often still are exposed in blood after other portions are completely covered by endothelium. As foreign matters, the protrusion portions exposed in blood will cause a rejection reaction of the human body and thus are an important inducement of the formation of inflammation and thrombus. Before the occlusion device is not completely covered by endothelial cells, a patient needs to continuously take anticoagulants, or there may be a risk of locally forming thrombus. The thrombus formed in the left atrium 12 may directly enter systemic circulation after falling off, so that it is likely to result in dangerous diseases such as apoplexia or acute myocardial infarction. Therefore, the disk of an occlusion device, especially a disk 31 placed in the left atrium 12, should have a flat structural characteristic and have no protrusion on the disk surface, most preferably a single-layer braided disk-shaped structure (hereinafter referred to as a single-layer disk). In comparison to the left atrium, when the second disk 32 in the right atrium 11 generates thrombus in the right atrium, the dangerous level of the thrombus will be far lower than that of the thrombus in the left atrium. Small thrombus will not cause an obvious danger or symptom after reaching the lung, while large thrombus will be likely to cause obvious damage to the lung. Therefore, the second disk 32 placed in the right atrium may be a double-layer fabric braided disk (a double-layer disk for short) in the prior art. In the double-layer disk in the prior art, a structure for connecting a conveying system is often provided on an outer side (a side away from the waist 33) of the disk. This structure will often from a protrusion portion 35 on the second disk 32. However, in the right atrium, it is widely believed that this is acceptable.

In addition, different individuals have different thicknesses of atrial spectra. Typically, the thickness of the upper side is larger, while the thickness of the lower side is smaller. As shown in FIG. 1, the thickness of the septum secundum 1 is obviously larger than that of the septum primum 2. This requires that the occlusion device have a flexible waist 33 which may allow the first disk 31 and the second disk 32 to relatively deflect at a certain angle and simultaneously allow a relative offset between the two disks in a section direction of the disks. If improvements are made to the prior art, the flexible waist 33 may improve the compliance of the whole occlusion device, so that it is advantageous for the fitting of the two disks to the walls of atrial spectra. The fine waist 33 occupies a smaller space, so it is advantageous for the fitting of two atrial spectra 1 and 2. If the rigidity of the waist of the occlusion device is high, the positions and angles of the two disks cannot be flexibly adjusted relative to each other. As a result, possibly, only one portion of a certain disk is fitted with the atrial spectra, while both inner and outer sides of the other portion of disk are exposed in blood. For example, in FIG. 1, if the first disk 31 and the second disk 32 cannot form a certain angle and thus are parallel to each other, a lower edge 37 of the first disk 31 cannot be closely clung to the atrial spectrum 2 or a lower edge 36 of the second sick 32 cannot be closely clung to the atrial spectrum 2. However, this portion separated from the atrial spectrum is often difficult to be covered by endothelium, resulting in the delay of endothelialization. Therefore, it is required to prolong the time of taking anticoagulants, and the local hemodynamics is thus influenced. Once the anticoagulants are stopped in the case of incomplete endothelialization, the risk of inducing thrombus is caused. If the placement of an occlusion device has a relatively obvious offset, the inner sides of two disks will be partially separated from the atrial spectra, thereby resulting in a higher thrombus risk. As can be seen, the flexible waist 33 may improve the overall performance of the occlusion device and reduces postoperative risks.

In the prior art, many braided occlusion devices do not have the two important features of a flat single-layer disk and a flexible waist. Occlusion devices braided from a plurality of braiding strands in the prior art will be briefly described below.

CN97194488.1 discloses an occlusion device, for example, a double-disk occlusion device 3 in FIG. 1. The occlusion device includes a support fabric having contractility. The support fabric constitutes a main body structure of the device, and a first disk 31 and a second disk 32 included in the main body structure and a waist 33 form an integral braided structure. One end of the braiding strands of the support fabric form the first disk 31, the middle portions of the braiding strands are gathered to form the waist 33, and the other ends of the braiding strands form the second disk 32. Both disks are of a double-layer braided structure. In order to achieve a practical occlusion effect, tens of elastic braiding strands are often required to weave the support fabric. As all the braiding strands densely pass through the waist 33, the waist has a high rigidity and is difficult to bend. Thus, the adjustable range of an angle between the two disks is very small, a relative offset cannot be realized along a disk surface direction, so that the two disks cannot better adapt to different anatomical structures and it is likely to result in insufficient fitting of disks and walls. Meanwhile, on the outer side of the first disk 31 of the occlusion device placed in the left atrium, the ends of the braiding strands are gathered and secured together to form a protrusion portion 34 on the first disk 31, so that the flat characteristic of the double-layer disk on one side of the left atrium is damaged. This protrusion portion 34 is often takes more time to achieve endothelialization than other portions and is even likely to be not completely endothelialized after the occlusion device has been implanted for several years. Typically, the patient undergoing this implantation operation will only take anticoagulants for half a year. Without anticoagulants, the non-endothelialized protrusion portion is likely to induce the formation of thrombus. In the article titled *A late complication of a patent foramen ovale amplatzer occlusion device*, Mohaned Egred, et al described an example in which thrombus was adhered onto the protrusion portion of the occlusion device after the occlusion device was implanted for many years.

The occlusion device disclosed by CN200780010436.7 may be regarded as an improvement on the basis of CN97194488.1. Their differences lie in that all tail ends of the braiding strands of the occlusion device disclosed in the former Chinese patent application are secured within a protrusion on the second disk 2, while there is no protrusion for securing the braiding strands on the first disk 31. That is, there is no convex structure protruding from the disk surface. The flat characteristic of the first disk 31 is improved. However, all the braiding strands of the occlusion device pass through the waist 33 twice, so the waist 33 has a higher rigidity and is difficult to bend.

The two occlusion devices described above in the prior art have a common feature that they are of an integral structure braided from braiding strands. A portion of a same braiding strand forms a first disk, another portion thereof forms a second disk, and a third portion thereof forms a waist. Such a design will certainly result in high rigidity of the waist. In the prior art, there also are split type occlusion devices braided from a plurality of braiding strands. These occlusion devices are characterized in that the braiding strands forming the first disk separately form this disk, but will not pass through the waist and participate in forming the second disk, the material of the waist is radically reduced, and this makes the optimization of the waist possible. However, in the prior art, the known occlusion device of a split type structure cannot have the features of a flat single-layer disk and a flexible waist connecting structure at the same time either.

US20040143291A1 discloses an occlusion device having a center post feature. This occlusion device includes two single-layer disks, each being constructed of a plurality of radially-arranged support rods and flexible occlusion device sheets adhered to the support rods, the support rods being braided from a plurality of braiding strands; and the two single-layer disks are connected by a center post having joints. A plurality of radial holes, through which the support rods constructing the single-layer disks are passed, are alternately arranged in the axial direction at two ends of the center post. The support rods on the single-layer disks are passed through different radial holes on the center post, to form a criss-cross arrangement. The thickness of the single-layer disk at the edge is equal to the diameter of the support rod. The thickness of the single-layer disk in its center is equal to the sum of diameters of the plurality of support rods. For example, when a single-layer disk is constructed of three support rods, the thickness of the single-layer disk in the center is at least equal to the sum of the diameters of the three support rods. Such a single-layer disk is lack of excellent flatness. However, in the absence of the center post, the support rods on a same single-layer disk are loosened, and cannot form an independent and stable disk-shaped structure. The center post of this occlusion device plays a role of, on one hand, connecting the two single-layer disks to form a waist, and on the other hand, restricting the support rods on the single-layer disks so that the single-layer disks form a stable disk-shaped structure. The center post is formed by connecting three rigid structures together in a manner as for joints, and is thus poor in flexibility. Furthermore, the tail end of the center post will protrude out of the outer side of the single-layer disk. Further improvement is required.

In conclusion, the braided occlusion devices in the prior art, regardless of one-piece structures or split-type structures, fail to have two important features simultaneously, i.e., flat single-layer disks and a flexible waist. For one-piece occlusion devices in the prior art, all braiding strands forming the first disk are passed through the waist to the second disk. As a result, the rigidity of the waist is absolutely too large due to intensive material in the waist. The ends of the braiding strands are intensively fixed to one or two points and those points often form a protrusion structure on the disk, and consequently, the flatness feature of the disk is damaged. For split-type occlusion devices in the prior art, the braiding strands are braided into a plurality of support rods first and the support rods are then connected to the center post to form an occlusion device. In the center of the disk where the support rods are overlapped, the thickness is significantly greater than the thickness of the edge, so that the flatness feature of the disk is damaged. In order to fix a plurality of separated support rods, the part of the center post, to which the supports are connected, requires a sufficient rigidity to restrict the location and direction of each of the support rods. This restricts the flexibility of the center post. As a result, the deformation part of the center post occurs at the joints, and self-adaptive deformation according to the particularly physiological structure of a patient is impossible.

SUMMARY OF THE INVENTION

Technical problems

One technical problem to be solved in the present invention is to provide an occlusion device having both key clinical demands, i.e., a flat occlusion disk and a flexible and simple waist.

Technical Solutions

To solve this technical problem, one technical solution as follows is employed. An occlusion device having an angle variable flat disk is provided, including a single-layer disk, a plug and a waist connecting the single-layer disk and the plug, the single-layer disk being braided from elastic strands and including a plurality of radially-arranged support rods, the grids braided elastic strands formed plug having a plurality of grids, the waist including at least one connecting strand; an annular interlocking structure with a hole is provided in the center of the single-layer disk, the plurality of support rods being connected into a flat integral body via the annular interlocking structure, the connecting strand of the waist being connected to the annular interlocking structure and the grids of the plug.

Preferably, the connecting strand of the waist passes through the hole on the annular interlocking structure, and passes through fabrics on the plug.

Preferably, the support rods of the single-layer disk are braided from elastic strands, and a cross-section of each of the support rods contains a group of two to eight elastic strands.

Preferably, there are four to eight support rods of the single-layer disk.

Preferably, the support rods of the single-layer disk are arranged in pair, each pair of support rods is located on a same diameter of the single-layer disk and braided from a same group of elastic strands, and the elastic strands of the support rods are braided together to form the annular interlocking structure.

Preferably, the group of elastic strands of the pair of support rods is divided into two subgroups, and the two subgroups of elastic strands bypass a central point from two sides of the central point of the annular interlocking structure.

Preferably, the support rods are bent into an L shape, S shape or arc shape.

Preferably, a section of each of the support rods close to a tail end is configured as a spring shape.

Preferably, a blunt tip is provided at the tail end of each of the support rods.

Preferably, the annular interlocking structure has a central hole.

Preferably, the single-layer disk is of a structure having an M-shaped cross-section and a convex center, the annular interlocking structure is convex toward the plug, and the tail ends of the support rods are folded to the plug.

Preferably, the single-layer disk further includes a first choke membrane, and the first chock membrane covers on the support rods and the annular interlocking structure.

Preferably, a securing device is provided on the plug, and the tail ends of the elastic strands of the plug are secured to the securing device.

Preferably, the securing device is provided thereon with threads for connecting or releasing the occlusion device.

Preferably, the plug comprises an inside fabric and an outside fabric, the inside fabric and the outside fabric being braided from common elastic strands, the inside fabric being located between the single-layer disk and the outside fabric and facing to the single-layer disk, the connecting strand of the waist being connected to the inside fabric, the securing device being disposed on the outside fabric.

Preferably, the inside fabric has a central mesh.

Preferably, the plug is disk-shaped or columnar.

Preferably, a second choke membrane is provided in the plug.

Preferably, the connecting strand of the waist is a closed loop.

Preferably, the connecting strand of the waist constitutes a plurality of independent closed loops.

Preferably, when the closed loops are stretched, a long axis of the closed loops is 2-10 mm.

Preferably, the diameter of the connecting strand is not more than 0.3 mm.

Preferably, fiber is adhered onto the connecting strand.

Beneficial Effects

Compared with the prior art, the present invention has the following advantages. The occlusion device has a flat single-layer disk and a flexible waist, and the single-layer disk has a function of self-adaptive regulation of morphology and is able to effectively adapt to different physiological structures while reducing complications. The flat single-layer disk is beneficial to decrease the risk of thrombosis and to quicken the endothelialization process. The flexible waist is helpful to fit the two disks to the wall of the heart or the vessel, reduce the disturbance to bloodstream, and reduce the hyperplasia of tissues. The presence of a single-layer disk having a function of adaptive regulation of morphology can reduce the reactive force to the surrounding tissues and decrease the risk of damaging the tissues.

BRIEF DESCRIPTION OF THE DRAWINGS

The present invention will be further described below with reference to the accompanying drawings and embodiments, in which.

DETAILED DESCRIPTION OF THE INVENTION

Preferred Implementations

To make the objects, technical solutions and advantages of the present invention clearer, the present invention will be further described in detail below with reference to the accompanying drawings and embodiments. It should be understood that, the specific embodiments disclosed herein are merely used for explaining the present invention instead of limiting the present invention.

The occlusion device disclosed in the present invention is of a split structure constituted of a plurality of braiding strands. Being formed by connecting a single-layer disk and a compressible plug by an independent waist, the occlusion device satisfies the two key clinical demands at the same time, i.e., a flat occlusion disk and a flexible and simple waist. The single-layer disk is constituted of a plurality of radially-arranged support rods, and an annular interlocking structure with a hole is provided close to the center of the single-layer disk. The annular interlocking structure is formed by braiding around the center of the single-layer disk by the braiding strands on the support rods, thereby avoiding concentrating a plurality of braiding strands in the center of the single-layer disk to cause the fold increase of the thickness of the single-layer disk and thus obtaining a very flat single-layer disk structure. Meanwhile, the annular interlocking structure fixes the relative positions of the support rods on the single-layer disk, so that the single-layer disk may become a stable and relatively independent integral body without requiring any additional material or structure for the purpose of fixation. The plug may be specifically implemented in various ways, similarly in manufacturing ways, with a significant difference in shaping molds. For example, for a PFO occlusion device, the plug may be a double-layer disk; while for a PDA occlusion device, the plug may be a cylindrical plug. The double-layer disk is a grid-type double-layer disk braided from a plurality of braiding strands and then shaped, with a fixed end on the outside fabric of the double-layer disk and a central hole on the inside fabric thereof, thereby forming a stable and independent integral body without the restriction of any additional material or structure. The cylindrical plug is braided from a plurality of braiding strands and also includes an inside fabric and an outside fabric, with a lateral side of the cylindrical plug being located between the inside fabric and the outside fabric. The inside fabric and the outside fabric are the bottom surfaces of the cylindrical plug, respectively.

As the single-layer disk and the plug have a respective stable and independent structure, the waist merely plays a role of connection instead of restricting the morphology of the single-layer disk and the plug. Therefore, the waist may be arranged to be simple and have a flexible structure to the maximum extent. For the occlusion device of the present invention, the waist between the single-layer disk and the plug is formed by passing a flexible connecting strand through the braiding holes on the single-layer disk and the plug and then connecting to the single-layer disk and the plug.

The occlusion device disclosed in the present invention has both features, i.e., a flat single-layer disk and a flexible waist. The structure of the occlusion device and its advantages when applied to occlude different human organ defects will be exemplified below by detailed description and several embodiments.

First Embodiment

Figure 2:
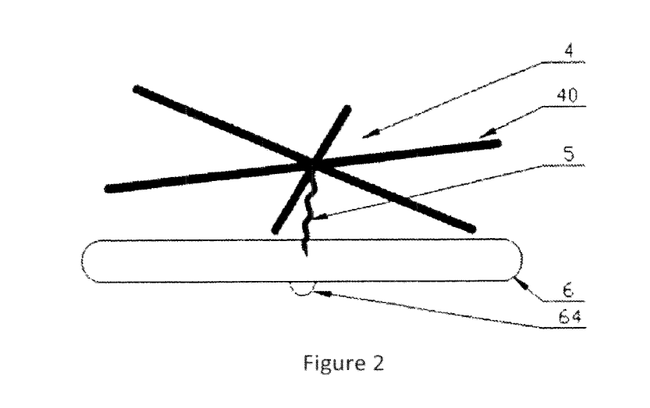
FIG. 2 is a simple diagram of one embodiment of an occlusion device according to the present invention.

FIG. 2 is a simple diagram of one embodiment of the occlusion device disclosed in the present invention. The occlusion device includes a single-layer disk 4 having six radially-arranged support rods 40, a braided grid-type double-layer disk 6 and a flexible waist 5. A fixed end 64 is provided in the center of the outside of the double-layer disk 6.

Figure 3:
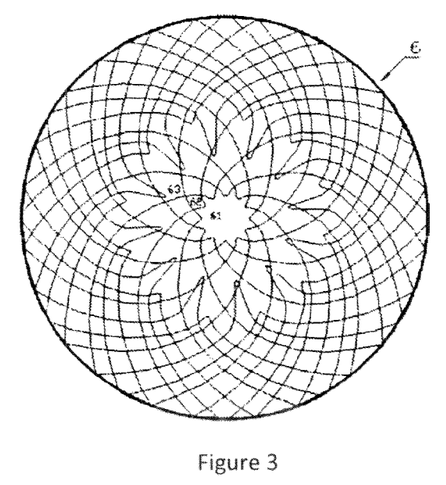
FIG. 3 is a top view of an inside fabric of a double-layer disk in one embodiment of the occlusion device according to the present invention.

The double-layer disk 6 of this occlusion device is of a disk structure, braided from a plurality of elastic braiding strands, where the two grid-type layers are parallel to each other. The double-layer disk 6 includes an inside fabric and an outside fabric in parallel to each other. The braiding may be made by a braiding method known in the prior art and then the resultant is shaped by a corresponding mold. Ends of the braiding strands forming the double-layer disk 6 converge to the fixed end 64 on the outside fabric (i.e., a side away from the single-layer disk 4) of the double-layer disk 6, and there is no ends of the braiding strands nor fixed braiding strand structure on the inside fabric of the double-layer disk 6 (i.e., a side adjacent to the single-layer disk 4), so that the space of the waist will not be used. In this way, the waist 5 may be made to be slender, loosened and flexible, which facilitates the adaptation of the occlusion device. FIG. 3 is a top view of the inside fabric of the double-layer disk 6. There is a central mesh 61 on the inside fabric of the double-layer disk 6 and a plurality of common meshes, for example, meshes 62 and 63. Those meshes may be provided for the waist 5 to pass therethrough. Membrane material may be provided in an interlayer between the inside fabric and the outside fabric of the double-layer disk 6, in order to assist in blocking the bloodstream.

The waist 5 of this occlusion device is formed of a flexible connecting strand. The connecting strand limits the maximum distance between the two disks, while allowing the swinging of an angle between the two disks and the relative displacement in the direction of the disk surface. The connection between the waist 5 and the double-layer disk 6 may be realized by passing the connecting strand through the meshes on the inside fabric of the double-layer disk 6. For example, one end of the connecting strand may be passed through the central mesh 61 on the double-layer disk 6 into the double-layer disk 6, and then out from the double-layer disk 6 from the mesh 63, and then knotted with the other end of the connecting strand, thereby forming a closed loop. During the production of this closed loop, three of the braiding strands forming the double-layer disk 6 are included into this closed loop. Therefore, the connection between the inside fabric of the double-layer disk 6 and the closed loop has a high strength. If the strength of a single braiding strand is large enough, a single one of the braiding strands forming the double-layer disk 6 may be selected for such a connection. For example, the single braiding strand is passed into the central mesh 61 and then out from the mesh 62. In this way, only one of the braiding strands forming the double-layer disk 6 is included into this closed loop. The resulting waist 5 is much looser. The selection of meshes on the double-layer disk 6 is not limited to the method as described above, and different combinations of meshes may be possible. There may be a plurality of closed loops; preferably, each of the closed loops is formed of a single connecting strand. In this case, the waist 5 still maintains sufficient flexibility. Particularly, even if a certain closed loop is damaged, the connection function by other independent closed loops will not be influenced. In this way, a redundant design is achieved. Alternatively, a single connecting strand may be passed through the holes on the single-layer disk 4 and the meshes on the double-layer disk 6 repeatedly to form a plurality of turns of closed coils. Such a design facilitates the improvement of the productivity.

Figure 4:
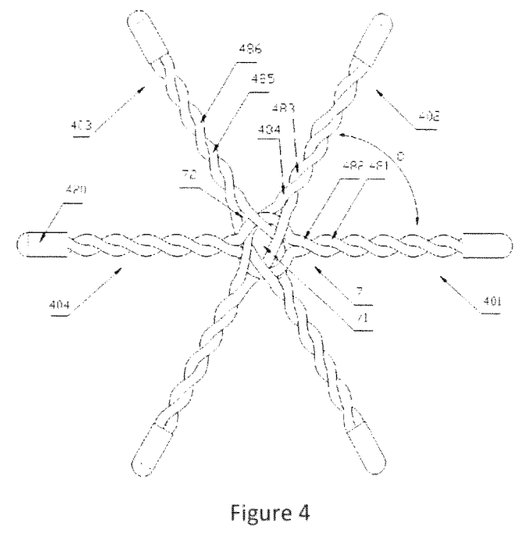
FIG. 4 is a schematic diagram of six radially-arranged support rods in one embodiment of the occlusion device according to the present invention.

The single-layer disk 4 of this occlusion device may include six radially-arranged support rods as shown in FIG. 4, wherein two support rods distributed on a same diameter form a pair of support rods, for example, a support rod 401 and a support rod 402 form a pair of support rods. Each pair of support rods is constituted of a group of elastic braiding strands. In this embodiment, each pair of support rods is comprised of two braiding strands forming a group of braiding strands. For example, the support rod 401 and the support rod 402 form a pair of support rods, and a group of braiding strands forming the pair of support rods includes a braiding strand 481 and a braiding strand 482. The specific production process will be described by taking the support rod 401 as an example. Two braiding strands 481 and 482 deriving from the tail end of the support rod 401 are braided to form the support rod 401; the two braiding strands are separated in the center of the single-layer disk 4; and, the braiding strand 481 spans over a braiding strand 485 deriving from a support rod 403, then under a braiding strand 486 deriving from the support rod 403, then over a braiding strand 483 deriving from another support rod 402, and then under a braiding strand 484 deriving from another support rod 402; therefore, the braiding strand 481 is sequentially overlapped with several braiding strands 485, 486, 483 and 484. Similarly, the braiding strand 482 spans under the braiding strand 483 deriving from the support rod 402, then over a braiding strand 484 deriving from the support rod 402, then over a braiding strand 485 deriving from another support rod 403, and then under the braiding strand 486 deriving from the support rod 403; therefore, the braiding strand 482 is sequentially overlapped with several braiding strands 483, 484, 485 and 486. The braiding strands 481 and 482 span cross a region near the center from the two sides of the center of the single-layer disk 4, and then again converge together to be braided to form a support rod 404. From FIG. 4, it can be seen that, in an annular region near the center of the single-layer disk 4, each braiding strand is sequentially overlapped with a plurality of braiding strands from other groups of braiding strands to form an annular interlocking structure 7 with a hole. The hole is formed naturally between the sequentially overlapped braiding strands. A central hole 71 may be reserved in the center of the annular interlocking structure 7. Through the annular interlocking structure 7, the positions of the six support rods are relatively fixed without requiring any additional material. The six support rods form an integral and flat single-layer disk 4, and a plurality of holes are formed in the annular interlocking structure 7, for example, hole 71 and hole 72, which is convenient for connection with the waist 5. During the braiding of the single-layer disk 4, the presence of the central hole 71 is also convenient for bypassing the braiding strand from the sides, which facilitates the improvement of the productivity. However, in another embodiment where quite soft braiding strands are used, at the end of braiding of the single-layer disk 4, the central hole 71 may be eliminated. Therefore, the feature inner diameter of the central hole 71 may be reduced to an extent so that only one connecting strand may be exactly passed through the central hole.

A preferred arrangement may be additionally provided at the tail end of the support rod, i.e., the tail end of the braiding strand. For example, a blunt tip 420 is provided at the tail end of the support rod 404 shown in FIG. 4. For example, the tail end of the braiding strand is wrapped by a flexible sheath and the sheath is fixed to the end of the support rod 404 by a soft suturing line. Alternatively, the tail end of the braiding strand is wrapped by an ePTFE thin film, and then heated and solidified to a blunt tip 420, or, tail ends of the braiding strands are welded together and then machined to a smooth blunt tip 420. This prevents sharp tail ends of the metal braiding wires from damaging the tissues.

Figure 5:
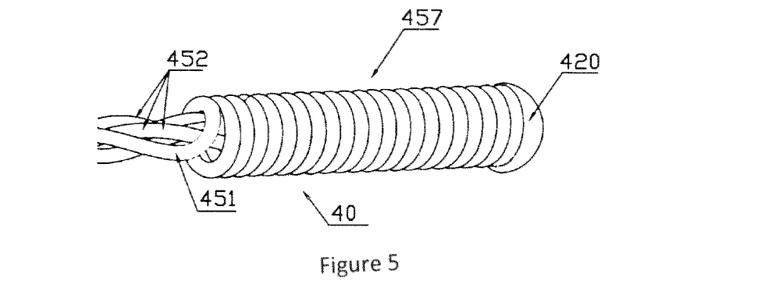
FIG. 5 is another embodiment of a support rod, wherein one braiding strand on the support rod is configured as a spring shape at a position close to the tail end of the support rod.
Figure 6:
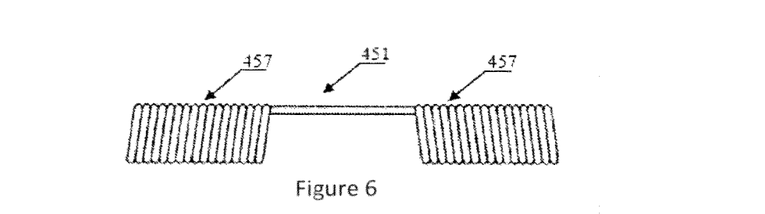
FIG. 6 is a schematic diagram of one braiding strand on a support rod.

In another embodiment of the support rod 40, as shown in FIG. 5, at the position close to the tail end of the support rod 40, a braiding strand 451 on the support rod 40 is configured as a spring shape, that is, a tail end spring 457 as shown in FIG. 5. Tail ends of other braiding strands 452 on a same support rod 40 are tied within a cavity of the tail end springs 457, and the tail end of the tail end spring 457 is machined to a smooth blunt tip 420. Specifically, the tail end springs 457 may be shaped on a same braiding strand in advance. As shown in FIG. 6, there is a tail end spring 457 respectively at two ends of the braiding strand 451. The braiding strand 451 having two tail end springs 457 forms, together with other braiding strands, a pair of support rods (including the support rod 40) and an annular interlocking structure 7, so that the pair of support rods constituted of braiding strands in a same group has better structural stability.

Figure 7:
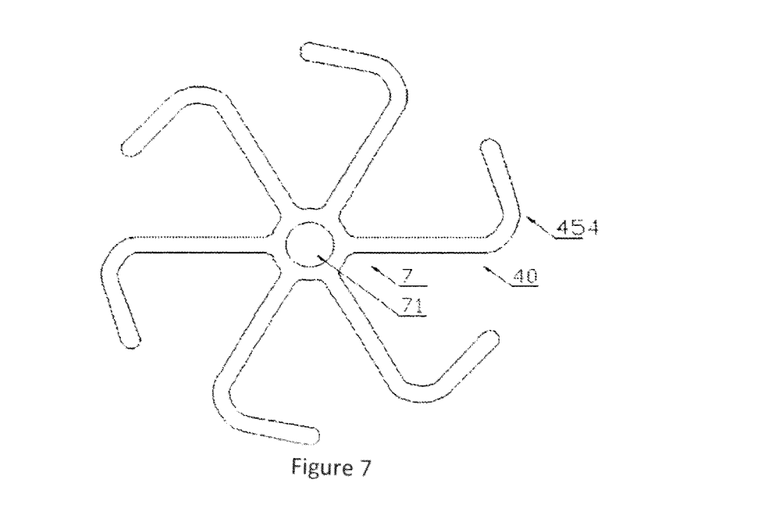
FIG. 7 is a simple diagram of another embodiment of a single-layer disk in the occlusion device according to the present invention.

Further, an L-shaped curved section 454, folded toward the circumferential direction, may be provided at an end of each support rod 40 of this single-layer disk 4, as shown in FIG. 7. Preferably, each L-shaped curved section 454 is substantially in the same plane as the single-layer disk 4. Preferably, the L-shaped curved section 454 is implemented by the tail end springs 457 as shown in FIG. 5 by a shaping treatment (not shown in FIG. 7). With such an L-shaped curved section 454, the tail end of the support rod 40 exhibits higher softness when a radial pressure is applied thereto. When the occlusion device is implanted into the heart, due to the beating of the heart, there is an interaction force between the occlusion device, particularly the support rod 40 of the single-layer disk 4, and the surrounding tissues. In this case, the L-shaped curved section 454 facilitates the increase of the contact area between the support rod 40 and the tissues, reduces the pressure applied by the single-layer disk 4 to the tissues, and decreases the risk of damaging the tissues. It is to be noted that, the support rod 40 may have an S-shaped curved section or arced curved section, and the curved portion of each support rod 40 is not limited to the tail end. Instead, the curved portion may be provided at any position of the whole support rod 40. The effect of such a curved portion is similar to that of the L-shaped curved section 454.

Figure 8:
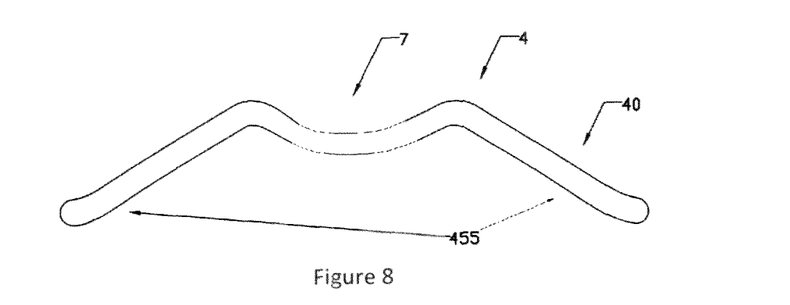
FIG. 8 is a diagram where a pair of support rods in the single-layer disk is bent into an M shape.
Figure 13:
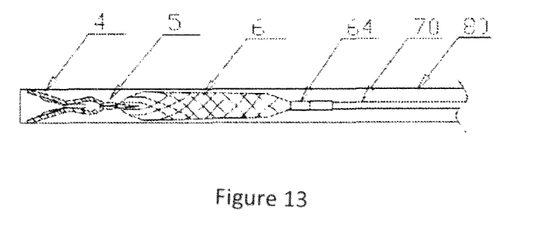
FIG. 13 is a diagram where the occlusion device according to one embodiment of the present invention is placed into a delivery sheath after being compressed.

Preferably, the single-layer disk 4 may be completely made of shape memory material, such as Ni—Ti alloy, and may be made into a disk shape having a convex center by thermoforming, for example, an M-shaped cross-section of the single-layer disk 4 passing through the central axis as shown in FIG. 8. That is, each pair of support rods is bent to be an M shape. The edge 455 (i.e., the tail end of the support rod 40) of the single-layer disk 4 is bent toward the double-layer disk 6 (not shown in FIG. 8), while the annular interlocking structure 7 in the center of the single-layer disk 4 is convex toward the center of the double-layer disk 6; furthermore, the edge 455 is closer to the double-layer disk 6 than the annular interlocking structure 7. Such a shape feature makes a distance between the edge 455 of the single-layer disk 4 and the double-layer disk 6 smaller than a distance between the centers of the two disks. This occlusion device ensures the proper length of the waist 5 (not shown in FIG. 8) and also makes the edges of the two disks closer to each other. This has the following advantages: on one hand, a proper length of the waist 5 is in favor of the flexibility of the waist 5 and allows a certain degree of displacement between the two disks in the direction of disk surface, and on the other hand, after the occlusion device is released, the edge 455 of the single-layer disk 4 clamps the interatrial septum more easily, thereby reducing the gap between the edge 455 of the single-layer disk 4 and the interatrial septum and decreasing the risk of thrombosis. The convex arrangement of the annular interlocking structure 7 toward the center of the double-layer disk 6 is useful to reduce the resistance when containing the single-layer disk 4 into the delivery sheath 80, as shown in FIG. 13.

Further, a flexible membrane is adhered to the braided single-layer disk 4, for example, sutured polyester or PTFE membrane, which may quickly block the bloodstream.

Second Embodiment

Figure 9:
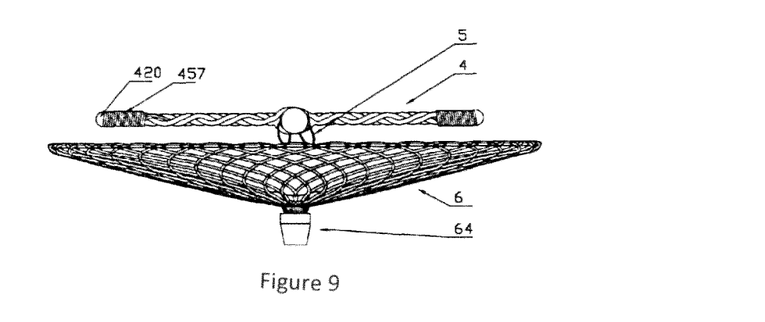
FIG. 9 is a side view of another embodiment of the occlusion device according to the present invention.

FIG. 9 is a side view of another embodiment of the occlusion device of the present invention. The occlusion device disclosed in this embodiment includes one single-layer disk 4, one double-layer disk 6 and a waist 5. Both the double-layer disk 6 and the waist 5 are similar to those in FIG. 2 and FIG. 3 in the first embodiment.

However, the connecting strands of the waist 5 in FIG. 9 are two independent closed loops, as a preferred implementation of the first embodiment. In another embodiment of the waist 5, one end of each of the connecting strands is only connected to a position near the center of the inside fabric of the double-layer disk 6 and the other end of the connecting strand is only connected to the single-layer disk 4, and this connecting strand is not a connecting strand having a front end connected to the tail end. One implementation of connecting with the double-layer disk 6 is that, one end of the connecting strand is passed through a plurality of meshes near the center of the inside fabric on the double-layer disk 6 and reaches the fixed end 64 of the outside fabric of the double-layer disk 6, to be fixed with the end of the braiding strand of the double-layer disk 6. As another implementation, the connecting strand may be passed through one or more meshes on the double-layer disk 6 and then knotted to be fixed on the cross point of two braiding strands of the double-layer disk 6. The connection between the connecting strand and the single-layer disk 4 is realized by passing one end of the connecting strand through at least one hole on the single-layer disk 4 and then fixing it on the single-layer disk 4 by winding together with a group of braiding strands of the single-layer disk 4; or the connection is realized as follows: after one end of the connecting strand is passed through one or more holes on the single-layer disk 4, this end of the connecting strand is knotted to form a knot having a size greater than that of a pore between the braiding strands of the single-layer disk 4, so as to prevent the connecting strand from falling from the corresponding hole on the single-layer disk 4. In addition, the connecting strand is passed through small holes on the single-layer disk 4 many times, and the friction force between the connecting strand and the single-layer disk 4 assists in fastening.

The waist 5 is soft, loosened and adjustable. The connecting strand thereof may be made of metal, for example, Ni—Ti alloy, stainless steel, platinum or the like. Preferably, Ni—Ti alloy is used, for example. Ni—Ti alloy has a shape memory property. Consequently, after the end is knotted and then the knot is thermally treated, the shape of the knot may be relatively stable, and the knot is less likely to become loose. The super-elasticity of the Ni—Ti alloy also may make the connecting strand softer and allow it to have sufficient tensile strength. The connecting strand may be non-metal, for example, nylon. A non-metal connecting strand is often softer than a metal connecting strand. Any one of the connecting strands may be formed of a plurality of fibers. When a metal connecting strand is used, in order to ensure an excellent flexibility, the diameter of this metal connecting strand is not greater than 0.3 mm. Preferably, the diameter of the connecting strand is less than 0.2 mm. In case of a connecting strand made of a plurality of fibers, the diameter of each fiber is not greater than 0.12 mm. Preferably, this connecting strand, the equivalent diameter of which is about 0.15 mm, is made of seven Ni—Ti alloy wires twisted together, each having a diameter of about 0.05 mm.

Particularly, the closed loops or coils made by the connecting strands may be stretched and deformed. When stretched maximally, each closed loop or each coil has a long axis vertical to the double-layer disk 6 or single-layer disk 4. The long axis is 2-10 mm, preferably, 3-5 mm.

Soft fibers may be adhered to the waist 5. The fibers are often polymer fibers, for example, PET, which may be wound or braided onto the connecting strands. Such fibers are useful to fill the human tissues to be repaired. For example, they are useful in assisting the occlusion of blood in a PFO passageway, reducing the residual shunts, and shortening the time required for occlusion.

Figure 10:
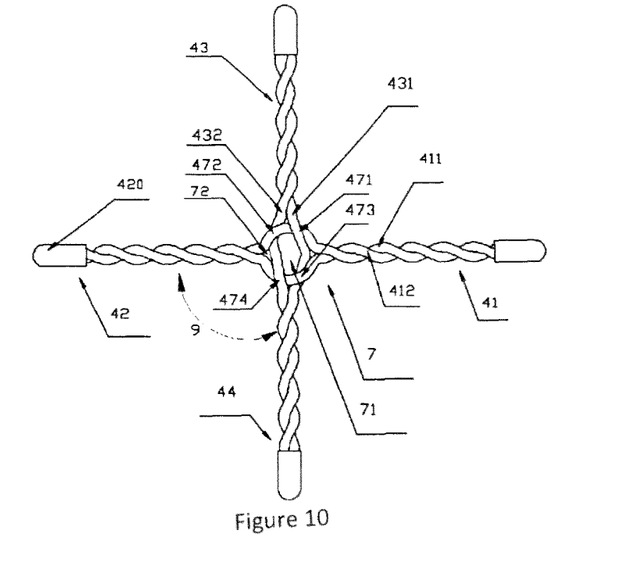
FIG. 10 shows four criss-cross radially-arranged support rods in the occlusion device according to the present invention.

Different from the first embodiment, the single-layer disk 4 may include four support rods, that is, two pairs of support rods. Among the crisscross radially-arranged four support rods 41, 42, 43 and 44 as shown in FIG. 10, each support rod is braided from two braiding strands. Two support rods 41 and 42 (or, support rods 43 and 44) on a same diameter of the single-layer disk 4 are formed of a same group of braiding strands. Ends of each group of braiding strands are fixed to the tail ends of the support rods 41, 42, 43 and 44, respectively, so that the ends of those braiding strands are fixed within the corresponding blunt tip 420, without being exposed to the outside of the support rods 41, 42, 43 and 44. Similarly to the method mentioned in the first embodiment, braiding strands belonging to different support rods 41, 42, 43 and 44 are sequentially overlapped near the center of the single-layer disk 4. An annular interlocking structure 7 is formed near the center of the single-layer disk 4, so that the positions of the support rods 41, 42, 43 and 44 are fixed with respect to each other, so as to form a very flat disk structure.

Specifically, a pair of support rods 41 and 42 distributed on the same diameter is braided from two braiding strands 411 and 412, and a pair of support rods 43 and 44 distributed on another diameter is braided from two braiding strands 431 and 432. The two braiding strands 411 and 412 forming the support rods 41 and 42, starting from the distal end of the support rod 41, are wound and braided together toward the center of the single-layer disk 4 in the radial direction. The two braiding strands 411 and 412 are separated from each other at a position close to the center of the single-layer disk 4. The two braiding strands 411 and 412, after bypassing the center point from the two sides of the center point, converge together at the other end of the diameter of the support rod 41, where they are interwoven together and extend toward a direction of a same diameter away from the center of the single-layer disk 4, to form the support rod 42. Also, another pair of support rods 43, 44 vertical to the first pair of support rods is also braided from a group of braiding strands 431 and 432. At a position close to the center of the single-layer disk 4, the four braiding strands are sequentially overlapped. Each braiding strand spans over a braiding strand from another group of braiding strands, and then spans under the other braiding strand from the another group of braiding strands. For example, braiding strand 411 spans over one braiding strand 431 from another group of braiding strands and then spans below the other braiding strand 432. The braiding strands 411, 412, 431 and 432 are sequentially overlapped with each other around the center of the single-layer disk 4, to form an annular interlocking structure 7, and to constitute an approximately circular or approximately polygonal central hole 71. In this annular interlocking structure 7, the braiding strand 411 has one cross point 471 and one cross point 472 with the braiding strand 431 and the braiding strand 432, respectively; and the braiding strand 412 has one cross point 473 and one cross point 474 with the braiding strand 431 and the braiding strand 432, respectively. From FIG. 10, it can be seen that the cross points 471, 472, 473 and 474 are distributed around the central hole 71 of the annular interlocking structure 7, instead of being stacked together. At each cross point 471, 472, 473 and 474, the thickness of the single-layer disk 4 is equal to the sum of diameters of the two braiding strands, being consistent to the maximum thickness on other positions of the single-layer disk 4 (substantially equal to the diameter of the support rods 41, 42, 43 and 44). Therefore, the annular interlocking structure 7 will not increase the thickness of the single-layer disk 4.

In FIG. 10, a group of braiding strands forming each pair of support rods includes only two braiding strands. As fewer braiding strands are included in each group of braiding strands, in the center of the single-layer disk 4, the braided central hole 7 looks irregular. In a different embodiment of the single-layer disk 4, if the number of braiding strands in each group is increased and softer braiding strands are used, the central hole 71 will be more circular or polygonal. Such an annular interlocking structure 7 has better structural stability and symmetry.

In this embodiment, as the thickness of the single-layer disk 4 in all parts is uniform and is almost the same as the diameter of the support rods 41, 42, 43 and 44, and the maximum thickness of the annular interlocking structure 7 in the center is substantially consistent to the maximum thickness of the single-layer disk 4, the thickness of the whole disk surface is uniform, without bumps obviously protruded from the disk surface, thereby ensuring an excellent flatness feature.

In another embodiment of the single-layer disk 4, there may be more than two braiding strands in each group of braiding strands forming each pair of support rods of the single-layer disk 4. There may be four or six or more braiding strands. It is assumed that each pair of support rods requires a certain rigidity, when the number of braiding strands forming each pair of support rods is relatively large, braiding strands having a small diameter may be used. In this way, the fatigue resistance is improved without increasing the diameter of the support rods (and without increasing the thickness of the single-layer disk 4).

Figure 11:
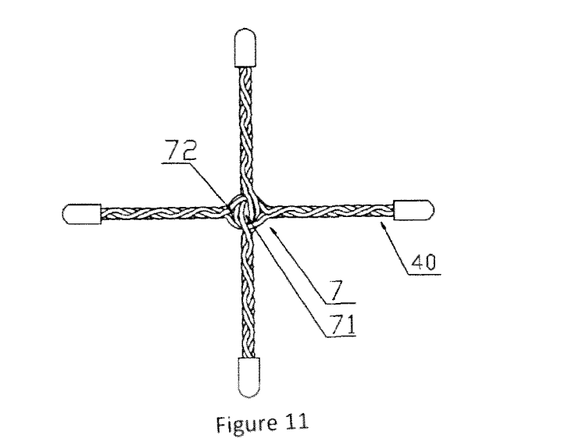
FIG. 11 is a diagram where each pair of support rods is braided from four braiding strands.

FIG. 11 shows an example where each pair of support rods is formed of four braiding strands. A group of braiding strands forming the support rod 40, starting from the distal end of one support rod, are braided to form one support rod 40. The braiding strands in this group are separated, at a position close to the center of the single-layer disk 4, into two sub-groups. Each sub-group includes two braiding strands. The braiding strands in the two sub-groups bypass the center point from the two sides of the center point, and converge together at the other end of the diameter of the support rod 40, where they are interwoven together and extend toward a direction of a same diameter away from the center of the single-layer disk 4, to form another support rod to which the support rod 40 is paired. Therefore, the support rods of the single-layer disk 4 may be braided in pair. Similarly, another pair of support rods vertical to the first pair of support rods is also braided from two sub-groups of braiding strands from another group. At a position close to the center of the single-layer disk 4, the four sub-groups are sequentially overlapped. Each braiding strand in a sub-group spans over a braiding strand from one sub-group of another group of braiding strands, and then spans under a braiding strand from the other sub-group of the another group of braiding strands. The braiding strands in the four sub-groups constitute a central hole 71 and form an annular interlocking structure 7. As there are lots of braiding strands and the gap between the braiding strands is smaller, the central hole 71 of the annular interlocking structure 7 is smaller, and the interlocking effect is improved.

The group of braiding strands in this embodiment includes four braiding strands. The braiding strands may be non-equally divided into two sub-groups. For example, one sub-group includes one braiding strands, while the other sub-group includes three braiding strands.

Further, there may be six, eight, ten or any other number of support rods forming the single-layer disk 4. Even if the number of support rods is different, there is no essential change in the braiding process of the single-layer disk 4.

It is to be noted that, there may be various ways of braiding the support rods from a plurality of braiding strands. The braiding way as shown in FIG. 11 is merely for ease of description, and will not be construed as any limitation to the present invention. Specifically, there are many ways of braiding a plurality of strands into a rod structure or a multi-strand structure, and those ways are well-known. Furthermore, when the number of braiding strands on each support rod is larger, the braiding technique is more flexible. The support rod may have a different cross-sectional shape by a different braiding technique. When a support rod has a non-rotationally symmetric cross-section, the cross-section has different moments of inertia in different directions. Therefore, the support rod exhibits different rigidities in different directions.

Figure 12:
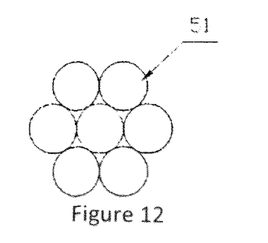
FIG. 12 shows a cross-section of another embodiment of the support rod, where each pair of support rods is constituted from seven fine braiding strands of the same diameter.

FIG. 12 shows a cross-section of another embodiment of the support rod. Each pair of support rods may be made of seven fine braiding strands 51 having the same diameter, so that the fatigue resistance of the support rod is improved. In the center of the single-layer disk 4, the seven braiding strands from one support rod are divided into two sub-groups, wherein one sub-group includes three braiding strands and the other sub-group includes four braiding strands. The diameters of the seven braiding strands 51 used may be the same or different. Each support rod may also be braided from six braiding strands. In this case, the diameter of a braiding strand in the center of the cross-section of the support rod may be slightly smaller than the diameter of the surrounding rest five braiding strands. Each support rod may also be braided from eight braiding strands. In this case, the diameter of a braiding strand in the center of the cross-section of the support rod may be slightly greater than the diameter of the surrounding rest seven braiding strands.

On a single-layer disk 4 having an annular interlocking structure 7, the angle between the support rods may have a proper self-adaptive regulation range. For example, in FIG. 10, the angle 9 between two support rods 42 and 44 may vary, and the profile of the single-layer disk 4 may be regulated to be elliptic from circular. Such self-adaptive deformation feature will become an important advantage for an occlusion device in some applications. Here, it is assumed that one pair of support rods 41 and 42 is fixed, and a circumferential force is applied to the support rod 43, this force being applied by the beating or deformation of the heart or vessel. It is assumed that the force is applied to the tail end of the support rod 43, a moment of force is generated to cause the support rods 43 and 44 to have a tendency of rotating clockwise. In the annular interlocking structure 7, two braiding strands 431 and 432 branched from the support rod 43 experience, at the cross points 471, 472, 473 and 474 where they are sequentially overlapped with the braiding strands 411 and 412, a friction force from the braiding strands 411 and 412. Generally, this friction force is unable to restrict the tendency of rotation of the support rods 43 and 44. Therefore, the angle 9 between the support rods 42 and 44 will decrease, and the profile of the single-layer disk 4 will not remain circularly symmetric, and instead, become an elliptical shape. Due to the deformation of the single-layer disk 4, the reactive force applied by the support rods 43 and 44 to the wall of the heart or vessel is reduced, and the risk of damaging the heart or vessel is decreased. As compared with FIG. 10, the number of support rods in the embodiment as shown in FIG. 4 is increased, the braiding strands for each support rod are sequentially overlapped with a greater number of braiding strands to form more cross points, the friction force applied to each support rod from other support rods increases too, the deformation resistance is enhanced, and the amplitude of the deformation will be reduced. In a case where the performance parameters and the moment of force of the support rods are substantially the same, the angle 8 between the support rods 401 and 402 in FIG. 4 is less likely to change than the angle 9 between the support rods 42 and 44 in FIG. 10. That is, a single-layer disk 4 formed of six support rods has better structural stability. In addition, if the number of braiding strands on each support rod is increased, the braiding strands in the annular interlocking structure will be more intensive, the friction force between the support rods will be greater, and the amplitude of motion of the support rods will be reduced. In different applications, the number of braiding strands, the number of support rods, and the braiding density of the annular interlocking structure 7 may be selected according to actual demands, in order to regulate the adaptation of deformation of the single-layer disk 4.

FIG. 13 shows the morphology of the occlusion device according to an embodiment of the present invention placed into a delivery sheath after being compressed. The single-layer disk 4 and the double-layer disk 6 are connected together by the waist 5, and a delivery steel cable 70 establishes a detachable connection with the double-layer disk 6 through the fixed end 64. The delivery steel cable 70 is pushed to release the occlusion device outside the delivery sheath 80. At this time, the occlusion device is expanded and recovered to a shape as shown in FIG. 2 or FIG. 9.

Third Embodiment

A PDA occlusion device in the prior art is often of a one-piece structure made of a plurality of braiding strands. There is one thick disk structure within the aorta, and it has no waist, so that the rigidity is often high. When the angle between the aorta and the arterial duct is small instead of approximately 90 degrees, the disk structure in the aorta often has a wrapped side and is thus unable to fit the wall of vessel well; furthermore, as the disk structure has a significant thickness and is not flat enough, great disturbance is caused to the bloodstream. The disk structure in the aorta is unable to deform self-adaptively, which also influences the wall fitting effect. When there is a large bloodstream obstacle in the aorta, impacting the obstacle by high-speed flowing bloodstream may rupture the blood cells and eventually cause serious complications.

Figure 14:
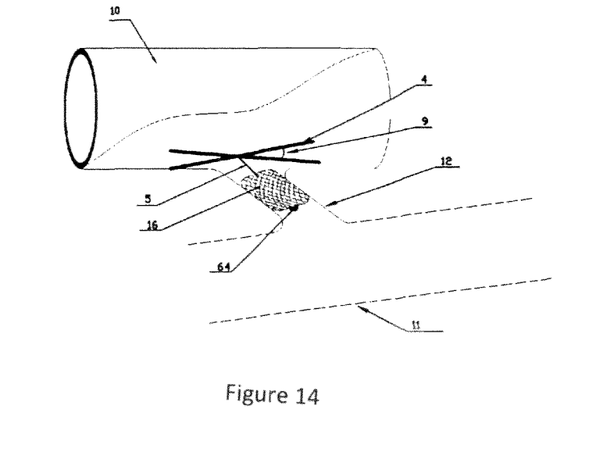
FIG. 14 is an arterial duct diagram where the occlusion device according to one embodiment of the present invention occludes the aorta.

In the above second embodiment, the double-layer disk 6 of the occlusion device may be arranged as a cylindrical plug 16 having a cylinder. The two bottom surfaces of the cylindrical plug are the inside fabric and the outside fabric, respectively. A membrane is provided inside the cylindrical plug 16, the membrane playing a role of blocking the bloodstream. Four support rods of the single-layer disk 4 are used for supporting and fixing the cylindrical plug 16, and a whole piece of flexible membrane may be covered on the four support rods. When applied in occluding PDA, the occlusion device of such a structure may exhibit significant advantages. As shown in FIG. 14, the flat single-layer disk 4 is tightly adhered to the inner wall of the aorta 10, and the cylindrical plug 16 is placed in the arterial duct 12. From FIG. 14, it can be seen that the axes of the arterial duct 12 and the aorta 10 are not vertical to each other, and the flexible waist 5 may allow the occlusion device to adapt to this vessel structure. On the other hand, the tightness of the braiding strands of the annular interlocking structure is optional, allowing the angle 9 between two support rods of the single-layer disk 4 to vary between 30° and 150°. In this way, the profile of the single-layer disk 4 may become elliptic from the originally circular profile. For a circular or rotationally symmetric single-layer disk 4, when a doctor places the occlusion device, he/she may not take the angle of release of the occlusion device into consideration. When the occlusion device is released into the aorta 10, the single-layer disk 4 is placed in the aorta. However, as the impact of the bloodstream in the aorta is great, the single-layer disk 4 covered by a membrane may be pushed into the arterial duct 12. At this time, the tubular aorta 10 squeezes the single-layer disk 4 so that the single-layer disk 4 deforms. In this way, the angle 9 between the support rods is changed, but the single-layer disk 4 may still maintain a good flatness.

Even if the single-layer disk 4 is not covered with a membrane, the support rods of the single-layer disk 4 may automatically adapt to the shape of the surrounding vessels and remain flat. At this time, the cylindrical plug 16 placed in the arterial duct 12 blocks the bloodstream. Meanwhile, as the pressure inside the aorta 10 is higher than the pressure inside the pulmonary artery 11, a thrust, in a direction from the aorta 10 to the pulmonary artery 11, is applied to the cylindrical plug 16; and this thrust is transferred to the single-layer disk 4 through the waist 5 so that a force is applied to the single-layer disk 4 to bring it to tightly adhere to the wall of vessel of the aorta 10 downwardly. As the aorta is of a tubular structure instead of a planar structure, in the plane of the single-layer disk 4, an extrusion force from the two sides to the center is also applied to the single-layer disk 4 by the aorta 10. This extrusion force may drive the angle 9 between the support rods on the single-layer disk 4 to change, for example, from preset 90° to 60°. With the change of the angle 9, the single-layer disk 4 exhibits an elliptic shape, and the direction of the long axis of the elliptic shape is consistent to the axial tendency of the aorta 10 in this place. Such self-adaptive regulation in morphology makes the single-layer disk 4 fit the wall of the aorta vessel better, thereby reducing the disturbance of the bloodstream. Furthermore, such self-adaptive deformation of the single-layer disk 4 weakens the reactive force of the support rods to the vessel, and reduces the damage to the tissues.

The foregoing contents are merely preferred embodiments of the present invention and not intended to limit the present invention. Any modifications, equivalent replacements and improvements made within the spirit and principle of the present invention should be included into the protection scope of the present invention.

The invention claimed is:

1. An occlusion device comprising:
a single-layer disk, a plug and a waist connecting the single-layer disk and the plug, the single-layer disk comprising a plurality of radially-arranged support rods and an interlocking structure, the plurality of radially-arranged support rods being braided from elastic strands, the plurality of support rods being connected into a flat integral body via the annular interlocking structure, all parts of the single-layer disk have a uniform thickness;
characterized in that in a region near to the center of the single-layer disk, each strand of one of the support rods is subsequently overlapped with the plurality of strands from other of the plurality of support rods such that the interlocking structure is formed.

2. The occlusion device according to claim 1, characterized in that a cross-section of each of the support rods contains a group of two to eight elastic strands.

3. The occlusion device according to claim 1, characterized in that the support rods of the single-layer disk are arranged in pair, each pair of support rods is located on a same diameter of the single-layer disk.

4. The occlusion device according to claim 3, characterized in that the group of elastic strands of the pair of support rods is divided into two subgroups, and the two subgroups of elastic strands bypass a center point from two sides of the center point of the annular interlocking structure.

5. The occlusion device according to claim 1, characterized in that the support rods are bent into an L shape, S shape or arc shape.

6. The occlusion device according to claim 1, characterized in that a section of each of the support rods close to a tail end is configured as a spring shape.

7. The occlusion device according to claim 1, characterized in that a blunt tip is provided at the tail end of each of the support rods, ends of the strands are wrapped with the blunt tip.

8. The occlusion device according to claim 1, characterized in that a distance between an edge of the single-layer disk and an edge of the plug is smaller than a distance between the center of the plug and the center of the single-layer disk.

9. The occlusion device according to claim 1, characterized in that the single-layer disk is of a structure having an M-shaped cross-section and a convex center, the annular interlocking structure is convex toward the plug, and the tail ends of the support rods are folded to the plug.

10. The occlusion device according to claim 1, characterized in that the single-layer disk further comprises a choke membrane, and the choke membrane covers on the support rods and the annular interlocking structure.

11. The occlusion device according to claim 1, characterized in that a securing device is provided on the plug, and the tail ends of the elastic strands of the plug are secured to the securing device.

12. The occlusion device according to claim 11, characterized in that the securing device is provided thereon with threads for connecting or releasing the occlusion device.

13. The occlusion device according to claim 11, characterized in that the plug comprises an inside fabric and an outside fabric, the inside fabric and the outside fabric being braided from common elastic strands, the inside fabric being located between the single-layer disk and the outside fabric and facing to the single-layer disk, the connecting strand of the waist being connected to the inside fabric, the securing device being disposed on the outside fabric.

14. The occlusion device according to claim 1, characterized in that the single-layer disk is connected with the plug via an independent waist.

15. The occlusion device according to claim 14, characterized in that the waist includes at least one connecting strand which connects the single-layer disk and the plug.

16. The occlusion device according to claim 14, characterized in that the waist includes at least a closed loop formed with a connecting strand.

17. The occlusion device according to claim 1, characterized in that the waist includes a plurality of closed loops, each of closed loop is formed from a single connecting strand, or the waist is comprised of a single connecting strand passed through the single-layer disk and the plug repeatedly to form a plurality of turns of closed coils.

18. The occlusion device according to claim 17, characterized in that a long axis of each maximally stretched closed loop or each coil is ranged from 2 to 10 mm.

19. The occlusion device according to claim 1, characterized in that the diameter of the connecting strand is not more than 0.3 mm.

20. The occlusion device according to claim 1, characterized in that flexible fiber is adhered onto the waist.

21. The occlusion device according to claim 1, characterized in that an angle of two neighboring support rods is self-adaptively varied between 30° and 150 °.

* * * * *